US012576211B2

(12) United States Patent
Grimmelikhuijsen et al.

(10) Patent No.: US 12,576,211 B2
(45) Date of Patent: Mar. 17, 2026

(54) REFILL SYSTEM FOR MEDICAL DEVICE USING JET DELIVERY PRINCIPLE

(71) Applicant: European Pharma Group B.V., Schiphol-Rijk (NL)

(72) Inventors: Frederik Jacob Christiaan Grimmelikhuijsen, Schiphol-Rijk (NL); Nickey Canton, Schiphol-Rijk (NL)

(73) Assignee: EUROPEAN PHARMA GROUP B.V., Schiphol-Rijk (NL)

( * ) Notice: Subject to any disclaimer, the term of this patent is extended or adjusted under 35 U.S.C. 154(b) by 816 days.

(21) Appl. No.: 17/995,811

(22) PCT Filed: Apr. 8, 2021

(86) PCT No.: PCT/NL2021/050229
§ 371 (c)(1),
(2) Date: Oct. 7, 2022

(87) PCT Pub. No.: WO2021/206553
PCT Pub. Date: Oct. 14, 2021

(65) Prior Publication Data
US 2023/0149630 A1 May 18, 2023

(30) Foreign Application Priority Data
Apr. 9, 2020 (NL) ..................................... 2025322

(51) Int. Cl.
*A61M 5/30* (2006.01)
*A61M 5/315* (2006.01)
(52) U.S. Cl.
CPC .......... *A61M 5/30* (2013.01); *A61M 5/31513* (2013.01); *A61M 5/31515* (2013.01)

(58) Field of Classification Search
CPC .......... A61M 5/31513; A61M 5/31515; A61M 5/31511; A61M 5/2448; A61M 5/284;
(Continued)

(56) References Cited

U.S. PATENT DOCUMENTS 1,563,627 A * 12/1925 Hein ........................ A61M 5/24
92/81
1,641,976 A * 9/1927 Laurent ................. A61M 5/204
604/184
(Continued)

FOREIGN PATENT DOCUMENTS

EP 1875934 9/2008
WO 0189613 A1 11/2001

*Primary Examiner* — James D Ponton
*Assistant Examiner* — Hong-Van N Trinh
(74) *Attorney, Agent, or Firm* — NIXON PEABODY LLP

(57) ABSTRACT

A fluid injection device of the jet stream type, comprising: —a housing defining a fluid collection chamber and having a nozzle; —a coupler for coupling the fluid injection device with a fluid container; —a piston head configured to be received and movable in the housing, to increase and decrease a volume thereof; —a piston rod, coupled to the piston head and having an internal flow channel, which extends from the piston rod for penetration of the fluid container, the piston head including a valve made of an elastically deformable material and comprising a radial flow channel, the radial flow channel being open when the piston head is moved in a fluid collection chamber volume increasing direction and the radial flow channel being closed by an elastic deformation of the valve material when the piston head is moved in a fluid collection chamber volume decreasing direction.

17 Claims, 11 Drawing Sheets

Figure 1:
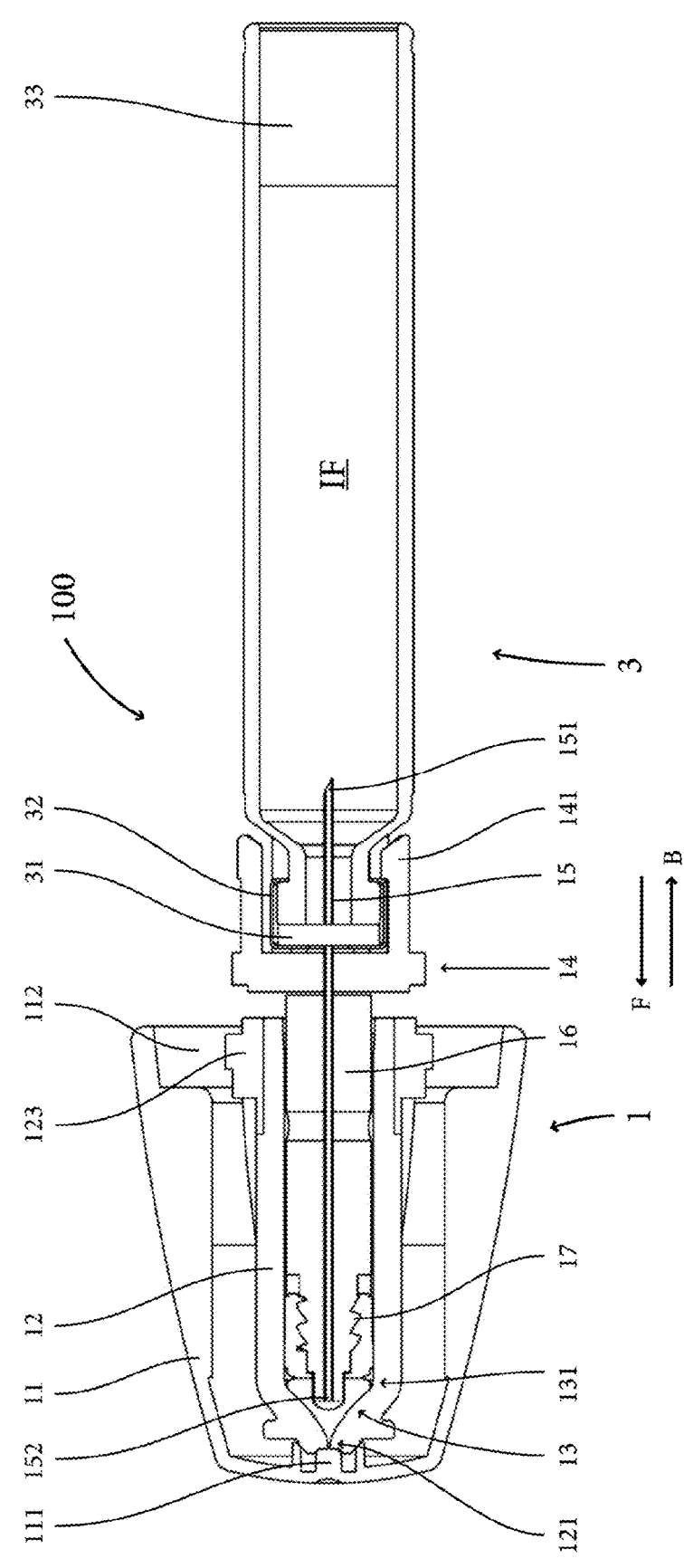

(58) Field of Classification Search
CPC . A61M 5/30; A61M 5/204; A61M 2005/2451
See application file for complete search history.

(56)                      References Cited

U.S. PATENT DOCUMENTS

| | | | | |
|---|---|---|---|---|
| 2,653,604 A * | 9/1953 | Hein, Jr. | ................. | A61M 5/30 |
| | | | | 604/68 |
| 2,821,193 A * | 1/1958 | Kish | ....................... | A61M 5/30 |
| | | | | 604/184 |
| 2,841,145 A * | 7/1958 | Epps | ..................... | A61M 5/284 |
| | | | | 604/89 |
| 3,425,413 A * | 2/1969 | Stephens | ................. | A61M 5/30 |
| | | | | 604/71 |
| 3,507,276 A * | 4/1970 | Burgess | .................. | A61M 5/30 |
| | | | | 604/68 |
| 4,153,186 A * | 5/1979 | Nye | .................... | F16K 15/1402 |
| | | | | 137/859 |
| 2014/0008366 A1 * | 1/2014 | Genosar | ............... | A61J 1/2096 |
| | | | | 220/265 |

* cited by examiner

REFILL SYSTEM FOR MEDICAL DEVICE USING JET DELIVERY PRINCIPLE

The present invention relates to a fluid injection device of the type that injects a fluid in a skin of a patient using the jet expulsion principle, as well as a fluid injection assembly.

Traditionally, fluids such as medicaments or bodily fluids are injected in skins of patients (human or non-human) using needles. Relatively recently however also so-called "needleless" fluid injection device have come to the market. Such devices inject a fluid in the skin of a patient by expelling the fluid from a tiny nozzle with a relatively high pressure, such that a jet stream expels from the nozzle. The jet stream is capable of penetrating the skin of the patient, successfully injecting fluid. Such a fluid injection device thus makes use of the jet expulsion principle and is of the type that injects a fluid in a skin of a patient using the jet expulsion principle. An advantage of such a fluid injection device is that "needlefear", common amongst patients, is overcome as no needle needs to be inserted in the skin of the patient to allow a fluid to be introduced therein. A further advantage of such device is that the fluid is absorbed at a higher rate by the skin of the patient, which is desirable for certain kinds of fluid.

For example US2005/0273048 A1 describes such a fluid injection device of the type that injects a fluid in a skin of a patient using the jet expulsion principle. A typical disadvantage of such fluid injection devices is that they need an accompanying adapter to allow the injection fluid to be aspired into the fluid injection device. Hence, before being able to inject a fluid, a user (patient) first needs to aspire the fluid in the fluid injection device from an external fluid container using the adapter. This is rather cumbersome, and not user-friendly. It also introduces risks related to contamination of the injection fluid. Devices similar to the one described in US2005/0273048 A1 are available on the market.

The patent literature describes some solutions to couple a fluid container with a fluid injection device of the type that injects fluid in a skin of a patient using the jet expulsion principle.

For example WO2005/051465 A1 describes a jet expelling assembly comprising a reservoir and an impulse chamber assembly. Between the reservoir and the impulse chamber is a conduit through which fluid can flow from the reservoir into the impulse chamber when a piston in the reservoir is moved. To prevent a backflow of the fluid from the impulse chamber back to the reservoir during injection of the fluid, in WO2005/051465 A1 the conduit has a "flow resistance" is "configured to allow" a backflow of less than 15%, preferably less than 10%, more preferably less than 5% and most preferably less than 1%. A first problem associated with WO2005/051465 A1 is that it does not disclose technical features to achieve this desired result. A second problem with WO2005/051465 A1 is that a backflow of 1% is regarded as too much, the desired backflow rate is 0%.

WO01/89613 A1 discloses an injector device for delivery of liquid from a high pressure source, the device comprising a housing, a pressure chamber comprising a pressure barrel for accommodation of at least one piston therein and having a front end opening for ejection of the liquid, the pressure chamber being of sufficient strength to sustain the liquid pressure, a piston inserted in the pressure barrel, a storage chamber, separate from the pressure chamber, for the liquid or the liquid precursor components, a conduit between the pressure chamber and the storage chamber, a pressurizing mechanism in the housing arranged to apply force, directly or indirectly, on the piston in the pressure barrel to create said liquid pressure, wherein the pressure chamber, the piston and the at least a part of the conduit are arranged as a unit, and wherein the unit and the housing have corresponding fitting parts allowing releasable attachment of the unit to the housing in a position permitting fluid connection between storage chamber and pressure chamber through the conduit and permitting the pressurizing mechanism to act on the piston.

U.S. Pat. No. 3,507,276 discloses a hypodermic jet injector comprising a housing member defining a jet orifice arranged in a blunt terminal position thereof, a first one-way valve formed within said housing member and operable to provide flow of the liquid to be injected to said orifice and to prevent backward flow through said valve, a member mounted for reciprocable movement with respect to said housing member, one of said members forming a cylinder and the other one of said members forming a cooperating piston within said cylinder to define a variable volume chamber of restricted cross section, one of said members including a second one-way valve communicating with said chamber and arranged to provide free flow of liquid to said chamber, said last-named member further defining an inlet passage for conveying liquid through said second valve to said chamber and including connections for a supply container of the liquid, said last-named member also defining a cartridge chamber for engaging and holding a pre-packed liquid cartridge of the type having a pierceable seal at the outlet end and a slidable rubber stopper at the opposite end and serving as the liquid supply container, said connections for the supply container including a canula with a hollow tip extending into the cartridge chamber adjacent to said second valve for piercing the seal at the outlet end of the cartridge, and a quick-release compression device comprising a spring engaged between said members and restrained by a latch supported by said housing member and engageable with said reciprocable member, a cocking lever pivotally mounted on said housing member and engaging said reciprocable member for moving said reciprocable member against the pressure of said spring to enlarge said chamber, said compression device being operable upon release of said latch to impart a fast and powerful movement to said reciprocable member in the direction to reduce the volume of said chamber to cause ejection of liquid from said chamber through said orifice with sufficient force to penetrate the skin of the patient.

EP 1 875 934 A1 discloses a prefilled medical drug expelling device comprising; a first and a second drug chamber, a nozzle comprising at least one expelling opening, a plunger forming a barrier between the first and the second drug chamber, at least one passage between the first and the second drug chamber, a prefilled drug being contained in the first chamber, wherein at least a rigid part of said plunger is in contact with the second drug chamber and wherein the plunger is adapted to be moved in a first direction, whereby the drug is transferred from the first to the second drug chamber, as well as a second direction, whereby the same drug is expelled through the expelling opening(s).

US2012/0059314 A1, which is regarded as the closest prior art, for the present invention, teaches an attachment for a standard injection device for needleless injection of a fluid, having a nozzle adapter and a piston unit. With respect to FIGS. 1 and 3 of this publication, the nozzle adapter comprises a skin contact surface arranged on the distal end thereof, having an outlet opening, a first cylinder section connecting proximally to the outlet opening and a second cylinder section connecting to the first cylinder section. The piston unit is mounted in a movable manner in the first cylinder section to form a piston-cylinder unit and the attachment has a fluid line for transporting fluid from the standard injection device to the outlet opening. More in particular, the fluid line comprises a piston, a sealing element and a transverse opening. The first cylinder section comprises first and second expansions. By moving the fluid line in and out of the first cylinder section, fluid can be aspired into a chamber behind the outlet opening and subsequently be expelled from said outlet.

Figure 3:
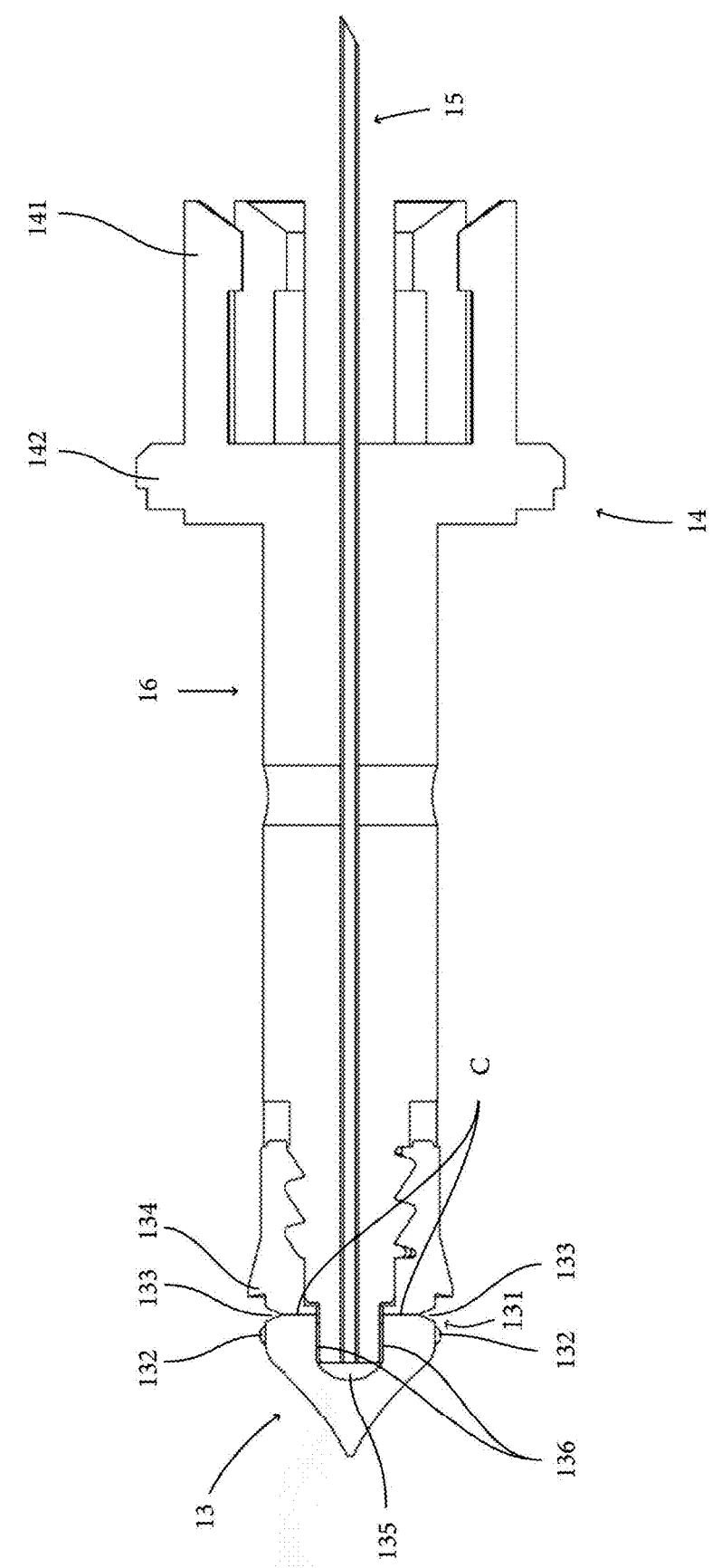

A first disadvantage of the device shown in FIGS. 1 and 3 of US2012/0059314 A1 is that the stroke length of the fluid line, and thus the volume of fluid to be injected, cannot be changed.

A second disadvantage of the device shown in FIGS. 1 and 3 of US2012/0059314 A1 is that a cylinder section comprising two expansions is relatively difficult to make, and therefore relatively expensive. Also the margin for production errors in manufacturing the cylinder section with expansions and the fluid line with piston and sealing element is very small as the sizes thereof must be closely matched.

Figure 4:
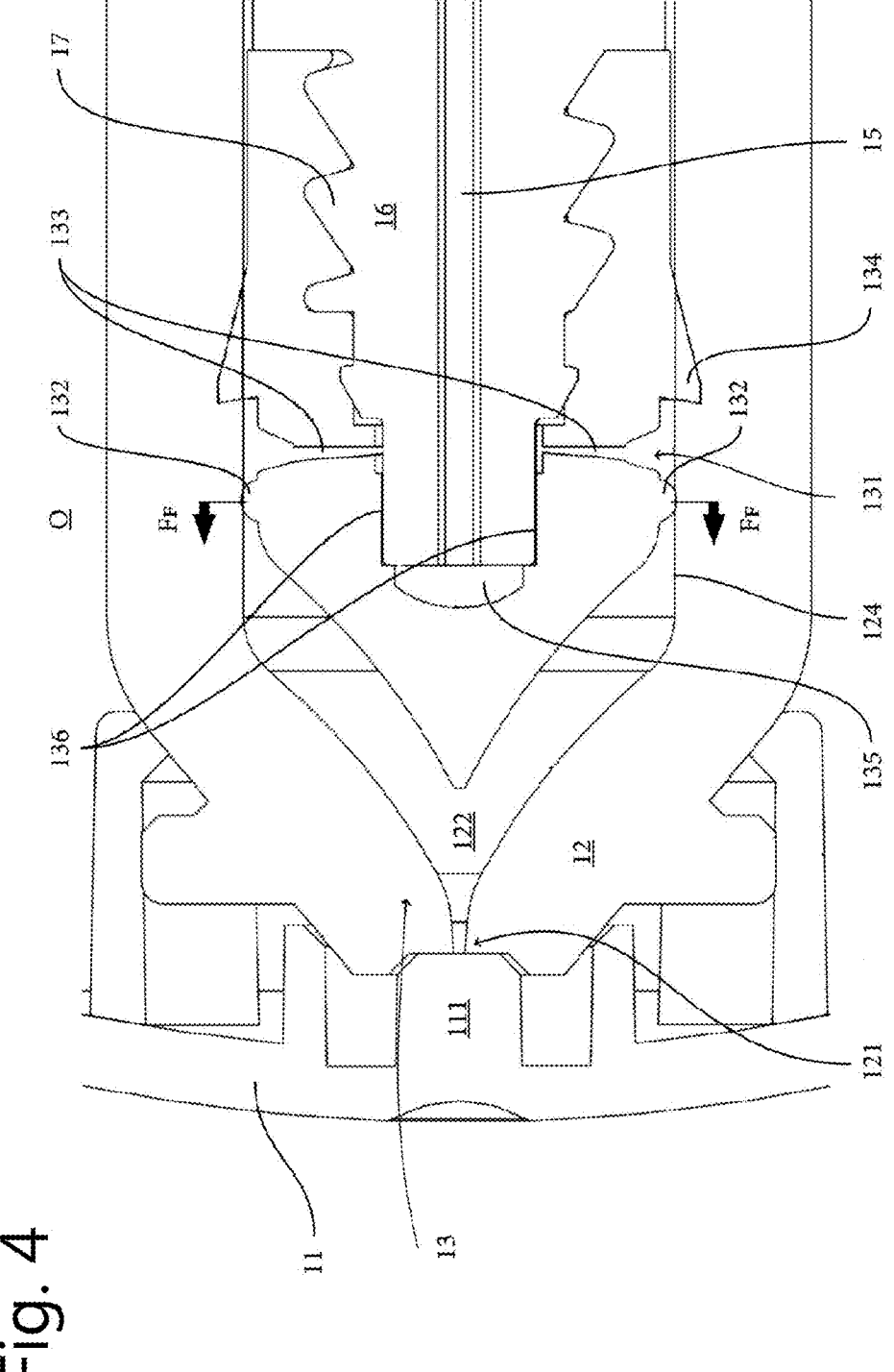

In FIGS. 4 and 6 of US2012/0059314 A1 alternative solutions using respectively a check valve and a ball valve are presented, the check or ball valve ensuring a low backflow rate during injection of the fluid.

A disadvantage of these solutions is that sufficiently low backflow rates could not be obtained when experimenting with these solutions. Furthermore, the solutions are relatively complex, leading to relatively high cost. It is also very difficult to match the shape of the tip of the plunger with the internal geometry of the nozzle, leading to possible backflow and an imprecise injection fluid amount. To obtain a sufficiently reliable sealing between the tip of the plunger and the internal geometry extremely small tolerances would be needed, leading to very high cost. Regarding the ball valve solution mainly, it is questionable at best how it performs when a shock or a sudden impact is applied to the injection device while injecting.

It is therefore an object of the present invention to provide an improved fluid injection device, which at least partially eliminates one or more of the above-mentioned disadvantages.

Accordingly, a fluid injection device of the type that injects fluid in a skin of a patient by ejecting a jet stream of fluid is provided. The fluid injection device comprises:

- a housing having an outlet nozzle, the housing defining a fluid collection chamber for collecting fluid to be ejected, the fluid collection chamber being in fluid communication with the outlet nozzle;
- a coupler for coupling the fluid injection device with a fluid container, preferably in a releasable manner;
- a piston head configured to be received in the housing, the piston head being movable in the housing to increase and decrease a volume of the fluid collection chamber; and
- a piston rod, coupled to the piston head and having an internal flow channel.

The flow channel of the piston rod extends with respect to said piston rod for penetration of the fluid container, so as to provide a flow path from said fluid container to said piston head.

Furthermore, the piston head includes a valve hat has an open and closed position, the valve being made of an elastically deformable material and comprising a radial flow channel that provides a flow path from the piston head to the fluid collection chamber, the radial flow channel of the valve being open when the piston head and piston rod are moved in a direction that increases the volume of the fluid collection chamber and the radial flow channel of the valve being closed by an elastic deformation of the elastically deformable valve material when the piston head and the piston rod are moved in a direction that decreases the volume of the fluid collection chamber.

The elastically deformable valve, in embodiments, advantageously provides an injection device which has a flowback rate of essentially 0%, i.e. which has a flowback rate of 0% or close to 0% such as between 0.5% and 0.001%. As the elastic deformation of the valve material ensures the closing of the radial flow channel, operation of the fluid injection device is very secure and reliable.

The elastically deformable valve, in embodiments, further advantageously provides an incremental dosing, allowing users to select virtually any amount of injection fluid between a minimum and maximum value, without being bound to limitations.

Advantageously, with the fluid injection device according to the present invention, the fluid container and the injection nozzle are coupled and fluidly connected in the same assembly. It is no longer needed to first aspire fluid in an injection chamber from an external fluid container using an adapter, but aspiring fluid in the fluid injection chamber (fluid collection chamber) can e.g. simply be done by turning a dial, switching a switch, pressing a button, or by performing another simple act on the outer shell of the fluid injection device. When injecting fluid, the fluid injection device and fluid container preferably remain coupled, the fluid container being arranged at the rear side of the fluid injection device compared to the location of the outlet nozzle.

The elastically deformable valve, which is to be inserted in the fluid collection chamber of the housing before the fluid injection device can be used, advantageously, allows relatively large production margins for manufacturing the housing and the valve as it is deformable.

The elastically deformable valve and the other components of the fluid injection device, in embodiments, further advantageously are relatively simple and cheap to construct, which provides commercial advantages. The fluid injection device is furthermore easy to use as the need for a separate adapted is omitted.

As explained in the above, the fluid injection device is of the type that injects fluid in a skin of a patient using the jet expulsion principle. In other words, the nozzle of the fluid injection device is needleless.

The piston head of the fluid injection device includes a valve. In embodiments, the piston head is formed as a valve, the entire piston head being made of the elastically deformable material. In other embodiment, the piston head comprises a valve as well as e.g. a rigid frontal plate or other rigid parts.

The piston can move in the fluid collection chamber, preferably along a longitudinal axis thereof. Hence, the internal volume of the fluid collection chamber is variable. Preferably, the internal volume of the fluid collection chamber is substantially zero after the fluid is expelled from the fluid collection chamber and when the piston is closest to the nozzle outlet.

In the open position of the valve, fluid can flow out of the internal flow channel of the piston rod, through the radial flow channels of the valve, and into the fluid collection chamber. Such a flow is also referred to herein as an "inflow". Preferably, there is an underpressure in the fluid collection chamber with respect to the fluid container to ensure a flow of fluid in the right direction An underpressure can e.g. be achieved by raising the pressure in the fluid container or by reducing the pressure in the fluid collection chamber. In the closed position of the valve the radial flow channels of the valve are closed by a deformation of the elastically deformable material, e.g. by a compression thereof, closing the radial flow channel, e.g. bringing the walls of the radial flow channel in contact with each other, and preventing the fluid to flow through the radial flow channels from the internal flow channel to the fluid collection chamber as well as from the fluid collection chamber back to the internal flow channel. Such a flow from the collection chamber back to the internal flow channel (and possible also back into the fluid container) is herein referred to as a "backflow" and is undesirable as the amount is injected fluid cannot be precisely determined when there is a backflow, and as backflow can cause a contamination of the injection fluid.

The valve is made of an elastically deformable material. The material is deformable/flexible enough to compress and close the radial flow outlets when the piston rod is moved towards the outlet nozzle. For example, the rod may be pushed with a relatively large force of up to 2000N, e.g. up to 1000N, such as about 500N. When the rod is of a (relatively) rigid material and the valve of an elastically deformable material, this may deform the material of the valve in a longitudinal and/or transverse direction to close the radial flow channels and prevent a backflow of the fluid in the fluid collection chamber. As will be described in the below, it is especially advantageous when a force is induced both in front of and behind the radial flow channels, e.g. due to friction between valve parts and the inner wall of the fluid container. However, while making use of the inventive concept underlying the invention, also other principles may be thought of which result in the same technical effect.

A further advantage of using an elastically deformable valve material is that the valve and the injection device may be used multiple times for the injection of fluid and are not disposable.

When the piston head is assembled in the housing and is moved in a direction away from the outlet nozzle, the fluid collection chamber is increased in volume and the radial flow channels of the valve are open. Fluid can flow from the fluid container into the fluid collection chamber. When the piston head is moved towards the outlet nozzle, the radial flow channels are closed and the fluid collected in the fluid collection chamber is expelled through the outlet nozzle in a jet stream, without any backflow.

In an embodiment of the fluid injection device, the valve is made of an elastomeric material or a rubber, e.g. a thermoplastic elastomer (TPE), a synthetic rubber or a natural rubber. These materials are some examples of the materials with the desired elastic deformation properties, to allow a smooth and simultaneously secure operation of the fluid injection device. However, many other materials would be suitable for this function. For example, a hardness of the valve material is between 70 and 100 Shore A, preferably between 80 and 100 Shore A, e.g. about 85 Shore A or about 90 Shore A or about 95 Shore A.

In an embodiment, the fluid injection device further comprising a cap configured to be coupled with the injector, e.g. with the housing, the cap including a seal for sealing the outlet nozzle. Preferably the cap is releasably coupled with the injector or housing. The seal and cap may e.g. protect and seal the outlet nozzle from the outside world when the fluid injection device is not used, e.g. preventing the introduction of dirt in the outlet nozzle and/or the fluid collection chamber. When the cap with seal is coupled with the injector, with the seal covering the outlet nozzle, and the piston moving backwards in the fluid collection chamber (backwards being: away from the outlet nozzle), a relative underpressure will be created in the fluid collection chamber. As a result of the underpressure therein, and the open state of the valve when the piston is moved backwards, fluid is able to flow from the fluid container into the fluid collection chamber when the piston is moved backwards. This is one possible way to "load" the fluid injection device and making it ready for an injection.

Preferably, the seal seals the outlet nozzle in a liquid- and air-tight manner when the cap is coupled with the injector. The cap and/or the seal may be replaceable.

In an embodiment of the fluid injection device, the piston head and the piston rod are coupled to each other via a threaded connection. For example, the piston rod is of a relatively stiff material, e.g. moulded polycarbonate plastic, possibly reinforced with glass fibre, or a metal. The piston rod and the piston head are preferably coupled in a manner which makes it possible to transfer forces introduced on the piston rod to the piston head and the valve, to open and/or close the valve. A threaded connection is one of many options which may be used to couple the piston head and the piston rod to each other in such a manner. In other embodiments, the piston rod and piston head are e.g. co-moulded, e.g. via a 2K injection moulding process.

In an embodiment of the fluid injection device, the piston head has a piston rod receiving chamber for receiving the piston rod therein, and the internal flow channel of the piston rod, when seen in longitudinal direction of said piston rod, extends beyond the threaded connection. Hence, in this embodiment the piston head is hollow to allow the piston rod to be received therein, e.g. coupled via a threaded connection. The piston rod has an internal flow channel that preferably extends along the entire length of the rod and mouths in the piston head and/or the valve. The valve then comprises a radial outflow opening through which the fluid can flow from inside the piston rod to a radial position outside of the piston rod.

In an embodiment of the fluid injection device, the piston head has a piston rod receiving chamber for receiving the piston rod therein, and the internal flow channel of the piston rod, when seen in longitudinal direction of said piston rod, extends beyond the location of the radial flow channel. In such an embodiment, the fluid, when flowing from the fluid container to the fluid collection chamber, first flows through the internal flow channel of the piston rod along a longitudinal direction of said piston rod, then mouths in a recess in the piston head, moves radially outside to a position outside of the piston rod, moves backwards with respect to the longitudinal direction of the piston rod at the outer side of the piston rod, and then further radially outwards through the radial flow channels of the valve. The fluid may then flow again in a longitudinal direction of the piston rod, past the piston head, and into the fluid collection chamber.

In an embodiment of the fluid injection device, the fluid container facing end of the flow channel has a sharp end configured for penetrating a septum of the fluid container. A septum is a standard seal of a fluid container containing a medical injection fluid. Such a septum may e.g. be easily penetrated with a needle. Hence, in embodiments, the internal flow channel of the piston rod is defined by a needle, the sharp end of the needle facing the fluid container. Therefore, even though the outlet nozzle of the fluid injection device is of the needle-less type, this does not imply per se that the fluid injection device as a whole is without any needle. In such an embodiment, the needle is however arranged at the back end of the fluid injection device, for penetrating a septum of a fluid container, not at the front end of the fluid injection device, for penetrating a skin of a user/patient. The needle may be fixed to the piston rod by a variety of manufacturing methods, including but not limited to e.g. gluing, ultrasonic welding, or injection moulding.

In an embodiment of the fluid injection device, the coupler between the housing of the fluid injection device and the fluid container comprises snap fingers for receiving the fluid container therein. This advantageously allows to renew a fluid container when one is emptied, as it is a releasable coupling. It is then only needed to renew the fluid container and not the entire assembly of fluid container and fluid injection device when a fluid container is empty.

In an embodiment of the fluid injection device, the coupler between the housing of the fluid injection device and the fluid container comprises a female Luer taper thread. A Luer taper thread provides a leak-proof connection, with which containers comprising a medical injection fluid are often fitted. To allow such containers to be coupled with the fluid injection device, the coupler may in embodiments comprises female Luer taper thread, so that the container with male Luer taper thread can be screwed in the coupler. Compared to a connection with snap fingers, a Luer lock connection may be more rigid and stiff. Of course, when the fluid container comprises a female Luer taper thread, the coupler may in embodiments comprise a male Luer taper thread.

In an embodiment of the fluid injection device, the valve further comprises a seal ring, positioned behind the radial flow channel of the valve when seen in a longitudinal direction of the piston rod, the seal ring being in contact with an inner wall of the fluid collection chamber. The seal ring advantageously prevents any backflow of fluid along an outer side of the piston rod when the piston head is moved forwards (i.e. towards the outlet nozzle) to inject fluid. The seal ring may e.g. be made of the same elastically deformable material as the valve, but this is not per se required, as long as the seal ring fluidly seal the area in between the inner wall of the fluid collection chamber and the valve to prevent the described backflow.

In an embodiment of the fluid injection device, the valve comprises an annular rim which is in contact with an inner wall of the fluid collection chamber with at least a part of its outer circumference. The annular rim is made of the elastically deformable material and has one or more throughflow openings, the annular rim being positioned in between the radial flow channel and the outlet nozzle when the piston is arranged in the fluid collection device. In use a forwards movement of the piston head results in a closing of the radial flow channel due to friction between the annular rim and the inner wall of the fluid collection chamber, while in use a rearwards movement of the piston head results in an opening of the radial flow channel due to friction between the annular rim and the inner wall of the fluid collection chamber.

The annular rim has throughflow openings to allow fluid to flow past the rim at least when "loading" the fluid injection device, i.e. when fluid flows from the fluid container to the fluid collection chamber. The throughflow openings may however also be open when fluid is injected, as the valve is closed at the radial flow channel(s). The throughflow openings may be embodied as recesses at the outer circumference of the annular rim. In such an embodiment, the annular rim is in contact with the inner wall of the fluid collection chamber with only a part of its outer circumference. The throughflow openings may in other embodiments however be arranged more radially inwards, the annular rim then contacting the inner wall of the fluid collection chamber with its entire outer circumference.

As the outer circumference of the annular rim contacts the inner wall of the fluid collection chamber, upon movement of the piston rod and piston head there is friction between these two components of the fluid injection device. This friction pulls open the radial flow openings when the piston rod and piston head are moved backwards. This friction simultaneously compresses and closes the radial flow openings of the valve when the piston rod and piston head are moved forwards.

A second aspect of the invention relates to a fluid injection assembly comprising a fluid injection device as described in the above as well as a fluid container, the fluid container being coupled to the fluid injection device via the coupler.

The container may e.g. be a syringe, a vial or a cartridge and may be any known container, e.g. comprising a medical injection fluid. One example of such a fluid is insulin, but many other fluids may be injected in the skin of a patient using the fluid injection assembly according to the second aspect of the invention.

In an embodiment of the fluid injection assembly, the fluid container comprises a piston head. By moving the piston head in a direction towards the fluid injection device, e.g. with an actuator, an overpressure in the fluid container may be obtained and the fluid therein is forced into the fluid collection chamber of the fluid injection device. This is one way of loading the fluid injection assembly for use by the user/patient.

Figure 2:
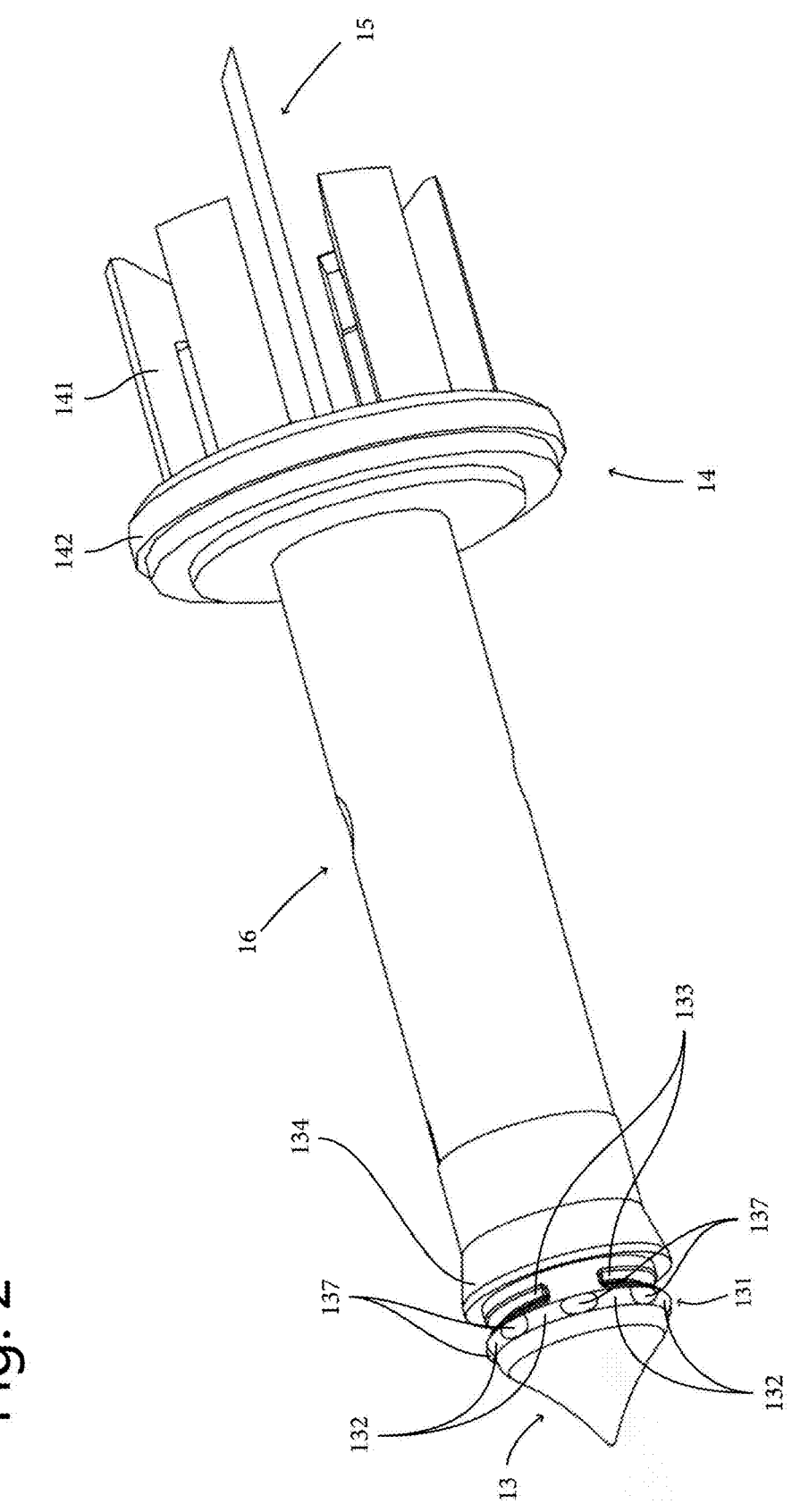
Figure 5:
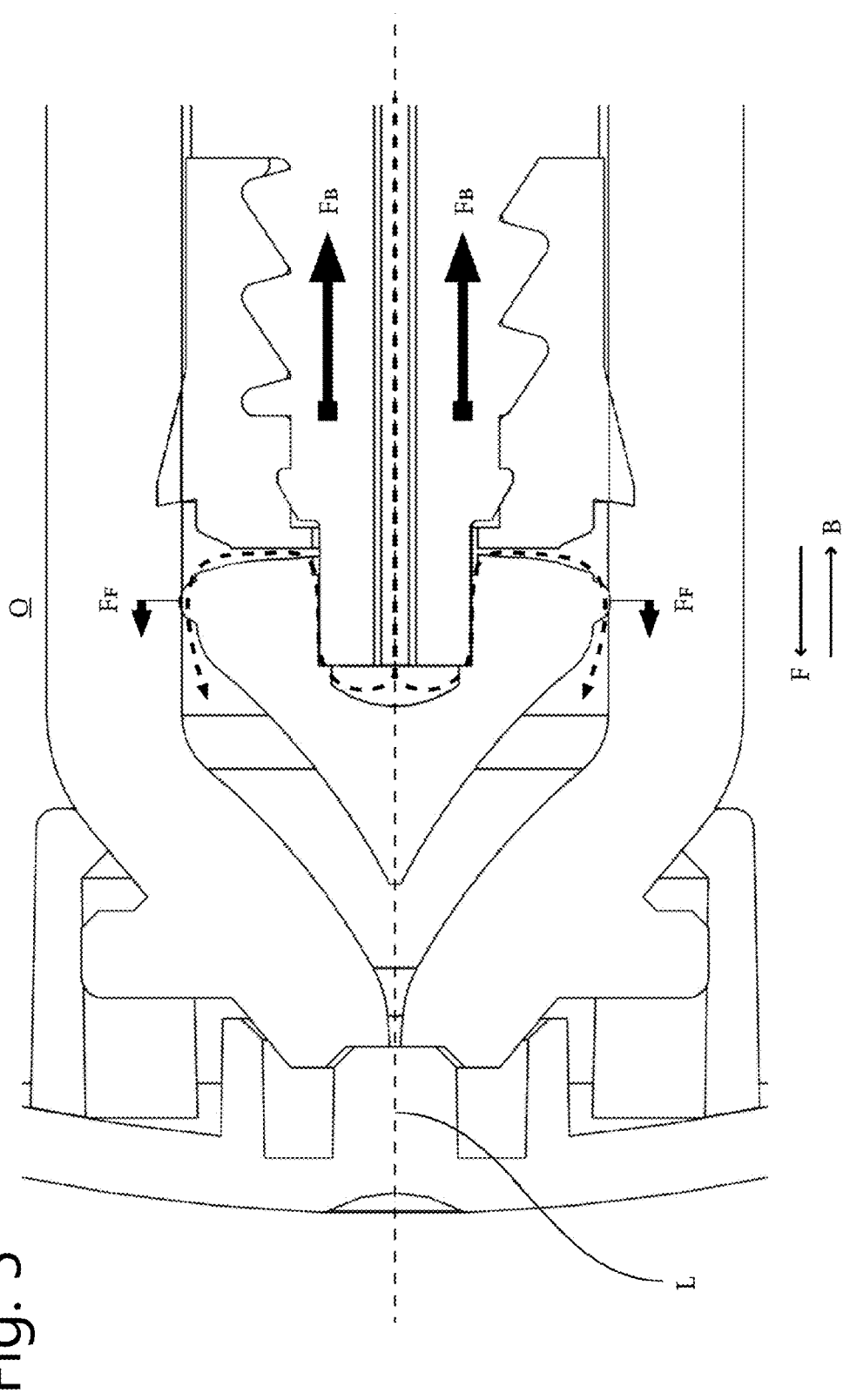
Figure 6A:
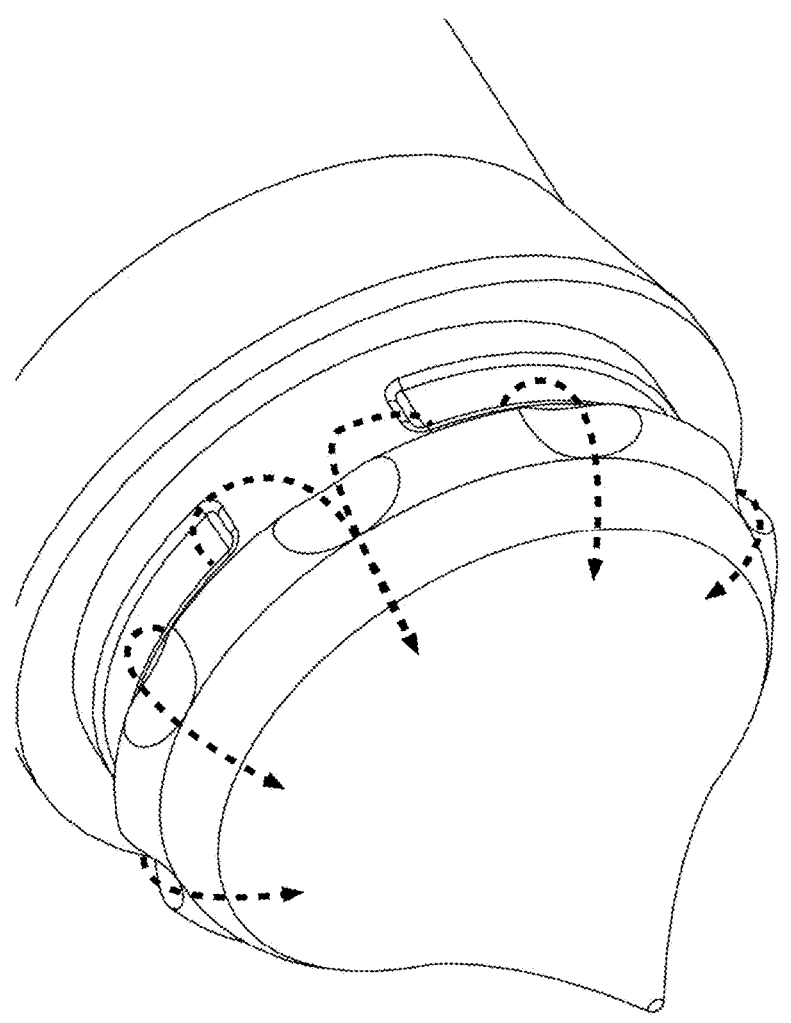
Figure 6B:
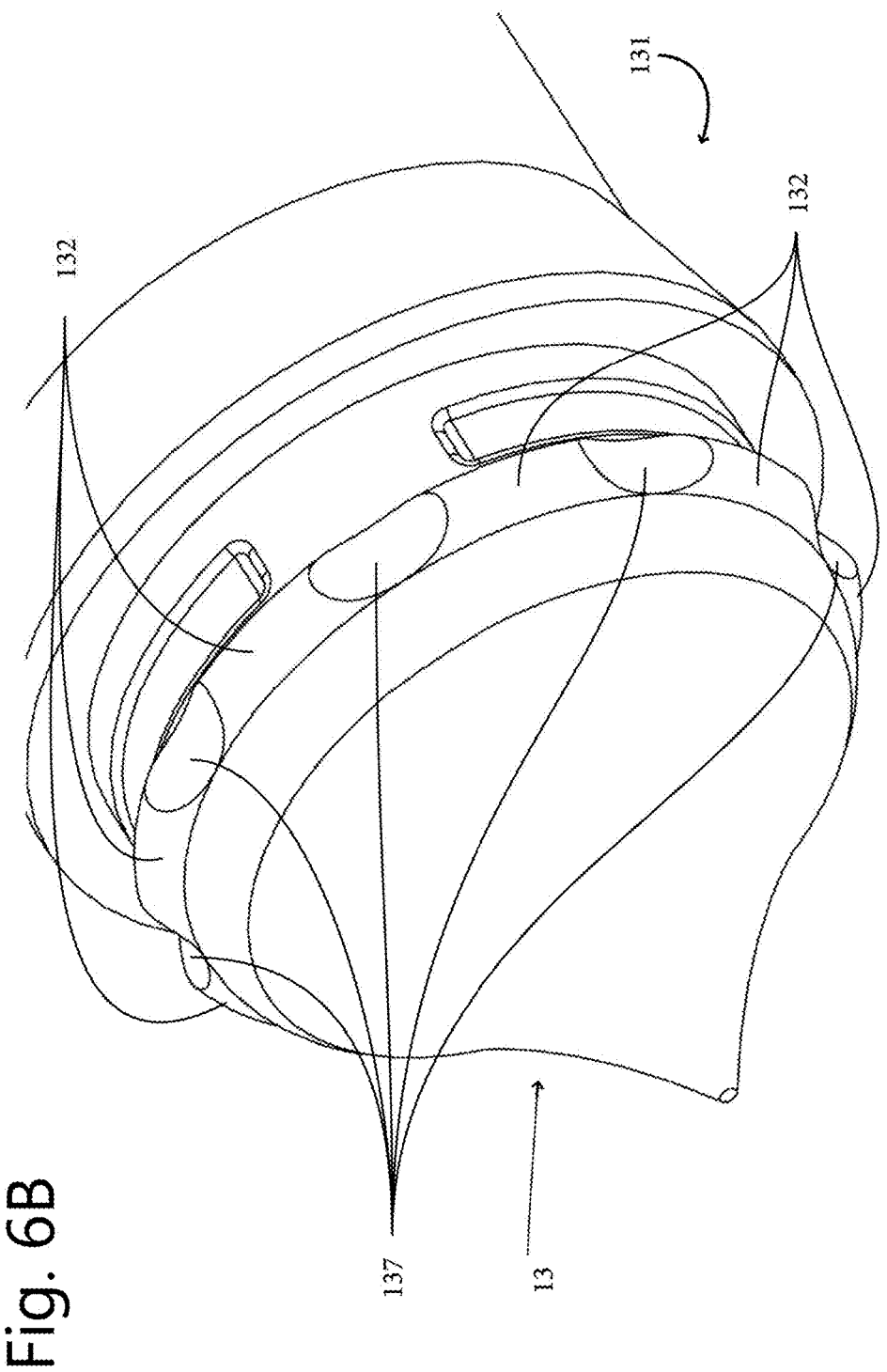
Figure 7:
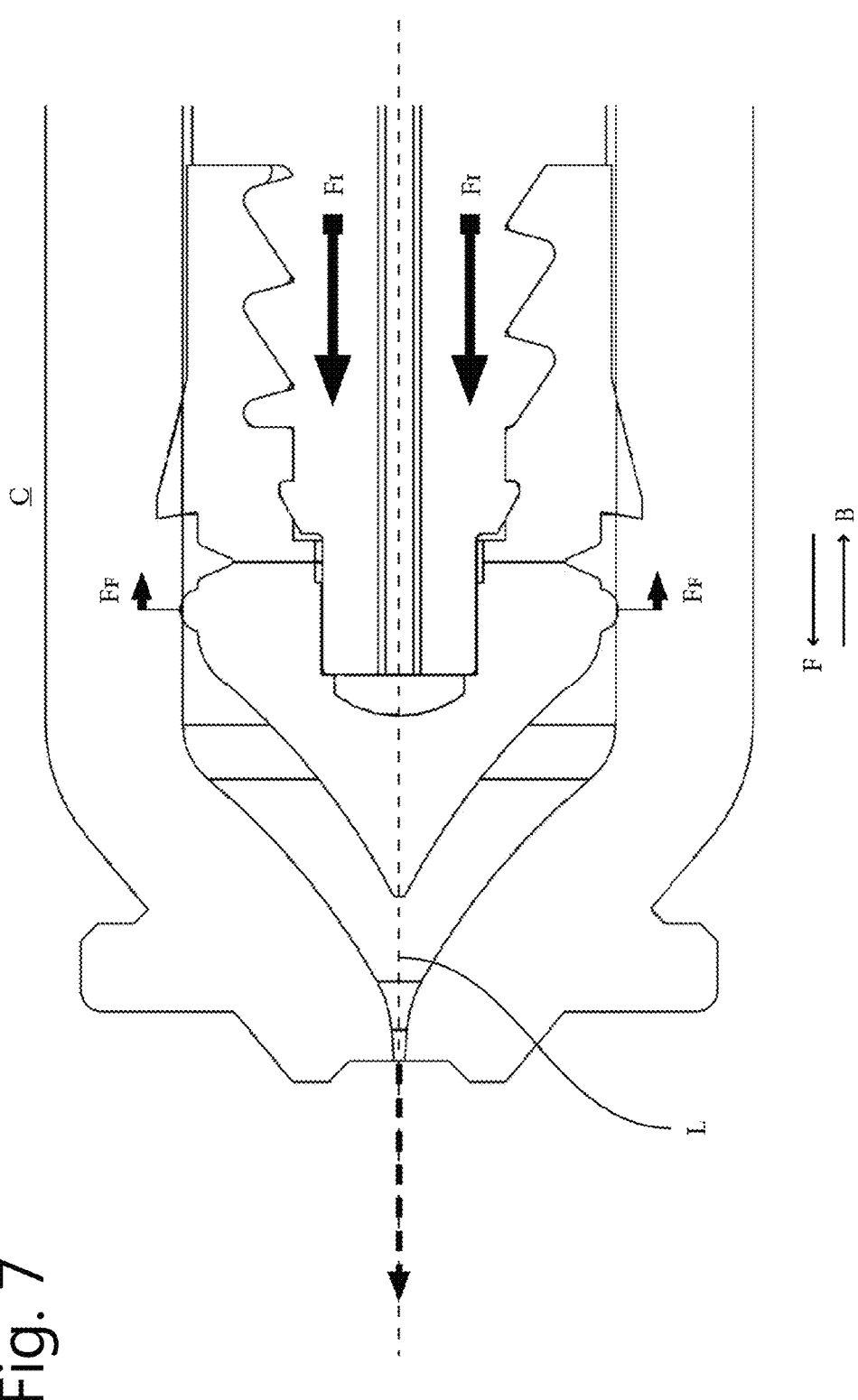
Figure 8:
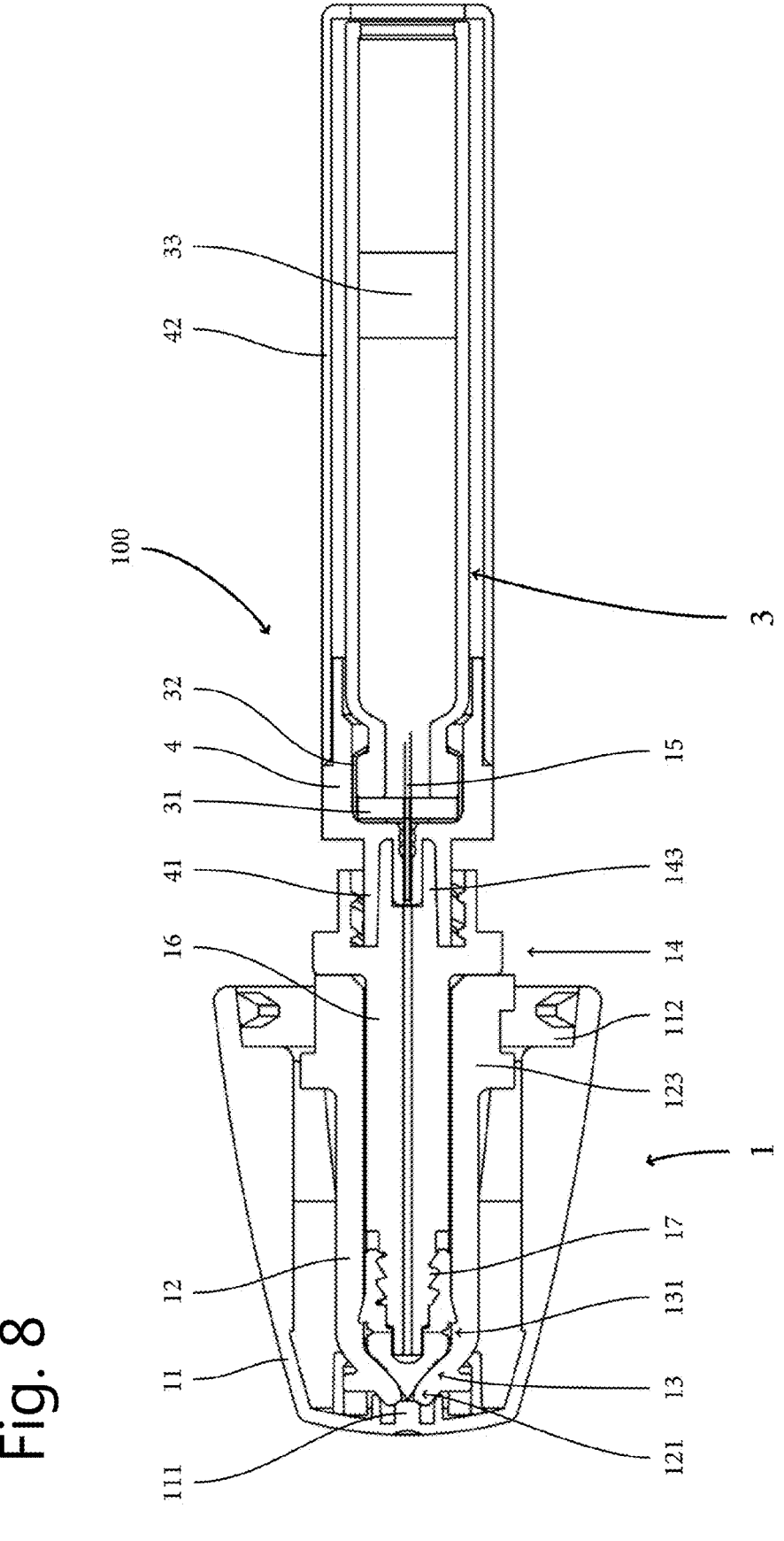
Figure 9:
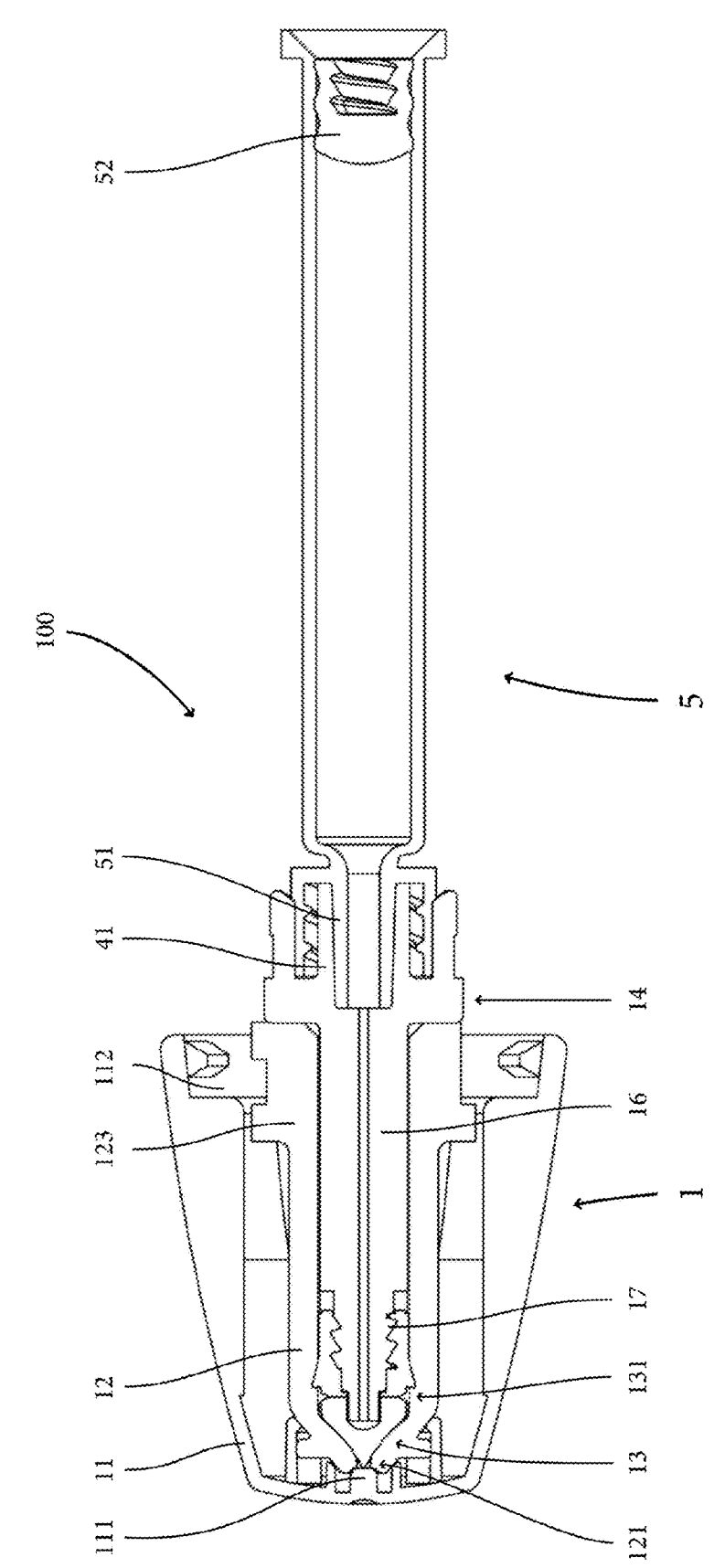
Figure 10:
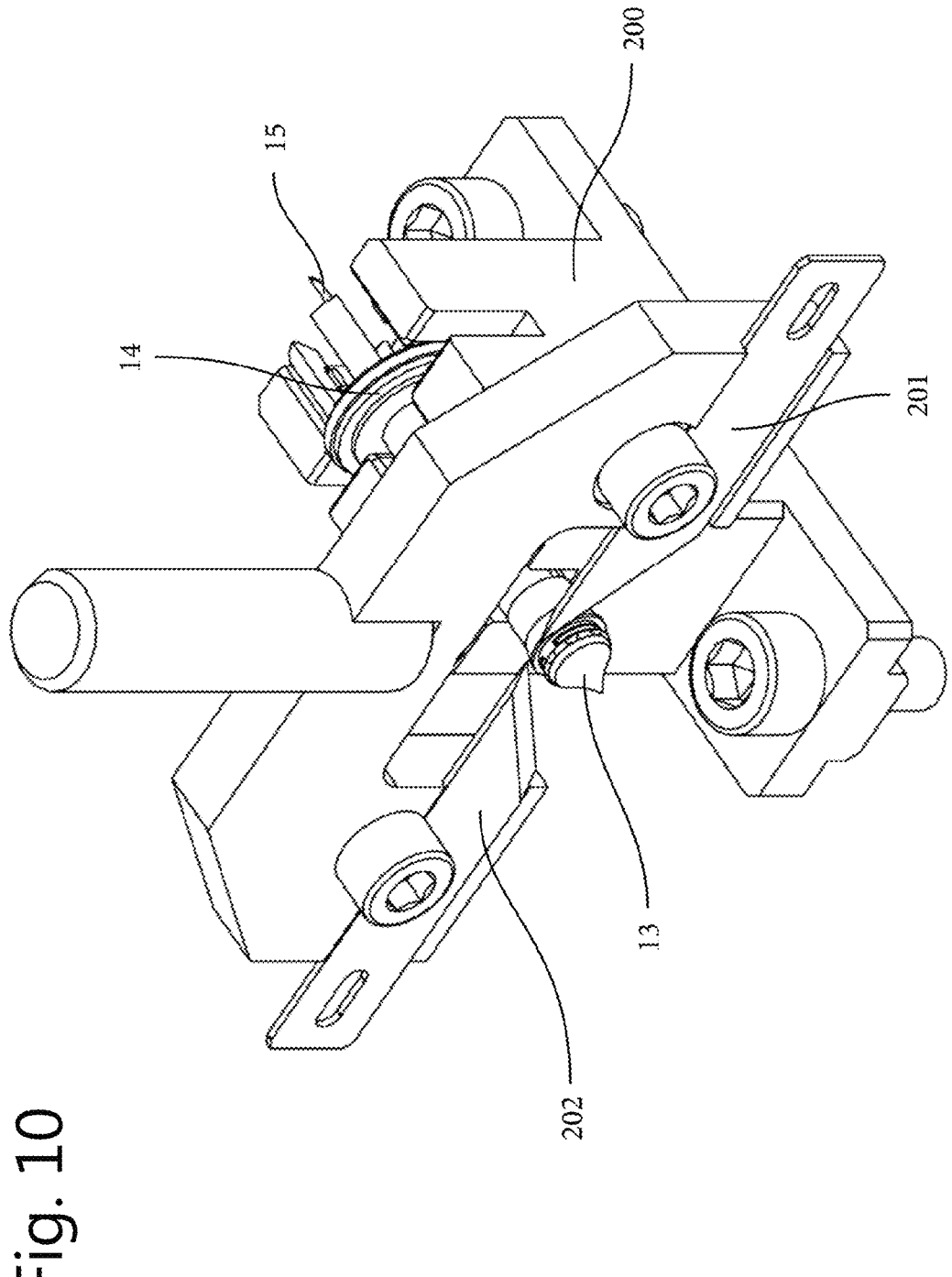

These and other aspects of the invention will now be elucidated further with reference to the attached Figures. The Figures will indicate like or same features with the same reference numerals. In these Figures:

FIG. 1 schematically shows a longitudinal cross-sectional view of a fluid injection assembly according to the present invention;

FIG. 2 schematically shows in isometric view a detailed view of the piston head, the piston rod, and the coupler of the fluid injection assembly of FIG. 1;

FIG. 3 schematically shows a longitudinal cross sectional view of the piston head, the piston rod, and the coupler of FIG. 2;

FIG. 4 schematically shows a view along a longitudinal cross section of the valve of the fluid injection device of FIG. 1, the valve being in open position;

FIG. 5 substantially corresponds to FIG. 4 and highlights the forces and the fluid flow;

FIG. 6A schematically shows in a front isometric view the fluid flow around an embodiment of a valve of the fluid injection device and assembly according to the present invention, the valve being in its open position;

FIG. 6B substantially corresponds to FIG. 6A but omits the fluid flow indications;

FIG. 7 schematically shows a view along a longitudinal cross section of the valve of FIG. 4, the valve being in a closed position;

FIG. 8 schematically shows a second embodiment of a fluid injection assembly according to the invention, in a longitudinal cross sectional view;

FIG. 9 schematically shows a third embodiment of a fluid injection assembly according to the invention, in a longitudinal cross sectional view; and FIG. 10 schematically shows one possible manufacturing process of the valve of the fluid injection device and assembly according to the present invention.

With respect to FIGS. 1, 2 and 3, which are described simultaneously, FIG. 2 shows a cross sectional view along a longitudinal axis of a fluid injection assembly 100. Shown in FIG. 2 is an isometric view of a part of the injection assembly, most importantly coupler 14, piston rod 16 and piston head 13 including valve 131. FIG. 3 shows the same elements as FIG. 3, but in a cross sectional view along a longitudinal direction.

The fluid container 3 and the fluid injection device 1 are coupled via coupler 14. The fluid container 3, as shown herein, comprises an injection fluid IF, a piston head 33 at the rear side thereof, a septum 31 to cover an outlet of the fluid container 3, and a cap 32 to seal the septum 31 with respect to the fluid container 3.

It is noted that this fluid container is a relatively standard fluid container. The present invention is in no way limited to the use of a specific fluid container. Indeed, FIGS. 8 and 9 show other embodiments of fluid containers, even though the three shown embodiments are certainly not the only types of fluid containers with which the fluid injection device may be coupled.

The coupler 14 of FIGS. 1, 2 and 3 here comprises snap fingers 141 for coupling the fluid container 3 to the fluid injection device 1. It is noted that the present invention is in no way limited by the type of coupling used between the fluid container 3 and the fluid injection device 1. The use of snap fingers 141 is only one exemplary option of a multitude of options. Indeed, with reference to FIGS. 8 and 9, a Luer coupling is e.g. shown.

The coupler 14 further includes a flange 142, extending radially outwards with respect to the piston rod 16. The piston rod 16 and piston head 13 may e.g. be moved by applying a force on the flange 142.

The fluid injection device 1 shown in FIG. 1 is here coupled with a cap 11 which may protect an outlet 121 of the fluid injection device 1 when the fluid injection device 1 is not used. The cap 11 comprises a seal 111 for sealing the outlet 121 in an air-tight and fluid-tight manner. The cap 11 is coupled to the fluid injection device 1 via coupling mechanism 112, 123 which comprises a male part 123 associated with the housing 12 and a female part 112 associated with the cap 11. In embodiments, the cap 11 may e.g. be coupled with a housing 12 of the fluid injection device 1.

The fluid injection device 1 shown in FIG. 1 comprises a housing 12. The housing 12 is hollow, as e.g. better visible in FIG. 5, and defines a fluid collection chamber. At a frontal end of the housing 12, a nozzle outlet 121 is defined. The nozzle outlet 121, and thus also the fluid injection device 1, is of the type that allows an injection of fluid in a skin of a patient by ejecting a jet stream of fluid.

The fluid injection device 1 shown in FIG. 2 also comprises a piston head 13. In an assembled state of the fluid collection device 1, the piston head 13 is received inside the fluid collection chamber. The piston head 13 is moveable in a forwards F and backwards B direction, thereby reducing respectively increasing a volume of the fluid collection chamber. The front side of the piston head 13 is matched to the shape of the fluid collection chamber near the nozzle outlet 121, allowing the piston head 13 to reduce a volume of the fluid collection chamber to substantially zero in its foremost position. The piston head 13 includes a valve 131, which is described in more detail in the below, with reference to FIGS. 4-7.

The fluid injection device 1 shown in FIG. 1 also comprises a piston rod 16, coupled to the piston head 13 via a threaded connection 17 and received in the fluid collection chamber of the housing 12. Upon movement of the piston rod 16, e.g. via flange 142, both the piston head 13 and the piston rod 16 move in the fluid collection chamber. The piston rod 16 comprises an internal flow channel 15 which extends in the backwards direction B with respect to the piston rod 16, and extends into the fluid container 3. The internal flow channel 15 provides a flow path from the fluid container 3, through the piston rod 16, and into the piston head 13. The flow channel 15 is here embodied as a needle, having a sharp end at the side facing the fluid container 3, allowing the needle to penetrate the septum 31 of the fluid container 3. Even though the connection between the piston rod 16 and the piston head 13 is here of the threaded type 17, many alternative connections between a piston rod 16 and a piston head 13 are known, and the invention is not limited to a particular type of connection.

As also shown with respect to FIGS. 2 and 3, the coupler 14 and the piston rod 16 may be made as one part.

With reference to FIGS. 2 and 3 mainly, piston head 13 includes a valve 131. The valve 131 as shown here includes a seal ring 134, radial flow channels 133, and annular rim 132 including throughflow openings 137. The valve 131 is made of an elastically deformable material, e.g. an elastomeric material such as a thermoplastic elastomer (TPE) or a rubber such as a synthetic rubber or a natural rubber. For example, the elastically deformable material of the valve 131 has a hardness of between 70 and 100 Shore A. In FIG. 3, the radial flow channels 133 are shown in their closed position C. Because of the elastic deformability of the piston head 13 material, the parts of the piston head 13 in front of the radial flow channel 133 and rearward of the radial flow channel 133 can move with respect to each other (and with respect to the piston rod 16) to open and/or close the radial flow channel 133.

The working of the valve 131 is now described in more detail, with reference to FIGS. 4-8 which are discussed together.

Shown in FIG. 4 is a more detailed view of the piston head 13 including valve 131, here in the open position O. The piston head 13 is coupled to the piston rod 16 via threaded connection 17. In the interior of the piston rod 16, a flow channel 15 is provided. The flow channel 15 extends between two ends of the piston rod 16, as the piston rod 16 is hollow. When a fluid container is coupled to the injection device, fluid can flow through said flow channel 15, as shown here. Piston head 13 comprises a piston rod receiving chamber 135 in which the piston rod 16 is received when the piston rod 16 and the piston head 13 are coupled. As shown here, the internal flow channel 15 runs along the entire length of the piston rod 16 and mouths in the piston rod receiving chamber 135 of the piston head 13 via a flow channel outlet arranged at a frontal side of the flow channel 15. When seen along a longitudinal direction of the piston rod, the flow channel outlet is arranged beyond the location of the threaded connection 17, and also beyond the radial flow channel 133.

As also illustrated in FIG. 5, the flow path of the fluid extends radially outwards from the piston rod receiving chamber 135, and backwards along an outside of the piston rod 16 through longitudinal flow channels 136, towards the radial flow channels 133. The fluid then flows radially outwards through radial flow channels 133, here in the open position O, and is forced past recesses 137 arranged in the annular rim 132 (see FIGS. 6A and 6B), into the fluid collection chamber 122. The annular rim 132 of piston head 13 includes recesses 137, here arranged on the radially outer side of the piston head 13, which serve as axial flow channels to allow fluid to flow from the radial flow channel 133 to the fluid collection chamber 122. A seal ring 134 prevents the fluid to flow in the backwards direction B again after is has flowed out of the radial flow channel 133.

As shown in FIG. 5, the valve 131 is in the open position O when the piston head 13 and piston rod 16 are moved in a backwards direction B, i.e. away from nozzle outlet 121 and increasing the volume of the fluid collection chamber 122. The open position O is here achieved by two forces which face in opposite directions. On the one hand, there is a friction force $F_F$ between the annular rim 132 of the valve 131 and the inner wall 124 of the fluid collection chamber, which are in contact with each other. On the other hand, there is a backwards pulling force $F_B$ effected by the backwards movement of the piston rod 16. The opposing forces result in an opening of the radial flow channel 133, and hence an opening of the valve 131.

In contrast, as illustrated in FIG. 7, when the piston rod 16 and piston head 13 are moved in a forwards direction F, towards the outlet nozzle and decreasing the volume of the fluid collection chamber, the valve is in the closed position C. An injection force $F_I$ deforms the part of the valve which is connected to the piston rod, while a friction force $F_F$ between the annular rim and the inner wall of the fluid collection chamber deforms the forward part of the valve. The combined effect of these deformations result in a compression and closing of the radial flow channel. Also the flow path from the piston rod receiving chamber to the radial flow channel may be compressed and closed to a more or less degree by these cooperating forces. As shown, as a result of the injection force, fluid is ejected from the fluid collection chamber through the outlet nozzle. Like in the open position of the valve, seal ring 134 prevents that the fluid flows in the backwards direction along a radially outer side of the piston rod when an injection force is applied on the fluid injection device, and ensures that all fluid collected in the fluid collection chamber is forced out of the fluid injection device.

FIGS. 8 and 9 schematically illustrate two alternative embodiments of a fluid injection assembly 100. In FIG. 8, coupler 14 of the fluid injection device 1 comprises a male Luer connector 143. This allows to couple the fluid injection device 1 with a fluid container 3 that is provided with a female Luer connector 41. For example, the fluid container 3 may be attached to an adapter 4, the adapter 4 comprising the female Luer connector 41.

In FIG. 9, the coupler 14 of the fluid injection device 1 comprises female Luer connector 41. This allows to couple the fluid injection device 1 with a syringe 5 that is provided with male Luer screw connector 51.

Shown in FIG. 10 is one possible way to manufacture a valve as described in the above. As shown in FIG. 10, a pre-moulded piston head 13, free of radial flow channels, may be fixed in a fixture 200. Knifes 201, 202 may then cut away some of the material of the piston head 13, to create the radial flow channel(s) at the desired location.

LIST OF REFERENCE NUMERALS

1 Fluid injection device
  11 cap
    111 seal
    112 coupling mechanism (female)
  12 housing
    121 outlet nozzle
    122 fluid collection chamber
    123 coupling mechanism (male)
    124 inner wall of fluid collection chamber 13 piston head
    131 valve
    132 annular rim
    133 radial flow channel
    134 seal ring
    135 piston rod receiving chamber
    136 longitudinal flow channel
    137 throughflow opening
  14 coupler
    141 snap finger
    142 flange
    143 male Luer connector
  15 internal flow channel
    151 fluid container facing end
    152 piston head facing end
  16 piston rod
  17 threaded connection
3 fluid container
  31 septum
  32 cap
  33 piston head
4 fluid container adapter
  41 female Luer connector
  42 container body
5 syringe
  51 male Luer taper thread
  52 stopper
100 assembly
200 fixture
  201 knife
  202 knife
B backwards direction
closed valve position
F forwards direction
$F_B$ force induced by movement in backwards direction
$F_F$ friction force
$F_I$ force induced by movement in injection direction
IF injection fluid
L longitudinal direction
O open valve position

The invention claimed is:

1. A fluid injection device of the type that injects fluid in a skin of a patient by ejecting a jet stream of fluid, the fluid injection device comprising:

a housing having an outlet nozzle, the housing defining a fluid collection chamber for collecting fluid to be ejected, the fluid collection chamber being in fluid communication with the outlet nozzle;

a coupler for coupling the fluid injection device with a fluid container;

a piston head configured to be received in the housing, the piston head being movable in the housing to increase and decrease a volume of the fluid collection chamber;

a piston rod, coupled to the piston head and having an internal flow channel, wherein the flow channel of the piston rod extends with respect to said piston rod for penetration of the fluid container, so as to provide a flow path from said fluid container to said piston head, and wherein the piston head includes a valve that has an open (O) and closed (C) position, the valve being made of an elastically deformable material and comprising a radial flow channel that provides a flow path from the piston head to the fluid collection chamber, the radial flow channel of the valve being open when the piston head and piston rod are moved in a direction that increases the volume of the fluid collection chamber and the radial flow channel of the valve being closed by an elastic deformation of the elastically deformable valve material when the piston head and the piston rod are moved in a direction that decreases the volume of the fluid collection chamber.

2. The fluid injection device according to claim 1, wherein the valve is made of an elastomeric material or a rubber, e.g. a thermoplastic elastomer (TPE), a synthetic rubber or a natural rubber.

3. The fluid injection device according to claim 2, wherein the elastomeric material or the rubber has a hardness of between 70 and 100 Shore A.

4. The fluid injection device according to claim 1, further comprising a cap configured to be coupled with the fluid injection device, the cap including a seal for sealing the outlet nozzle.

5. The fluid injection device according to claim 4, wherein the seal seals the outlet nozzle in a liquid- and air-tight manner when the cap is coupled with the fluid injection device.

6. The fluid injection device according to claim 1, wherein the piston head and the piston rod are coupled to each other via a threaded connection.

7. The fluid injection device according to claim 6, wherein the piston head has a piston rod receiving chamber for receiving the piston rod therein, and wherein the internal flow channel of the piston rod, when seen in longitudinal direction (L) of said piston rod, extends beyond the threaded connection.

8. The fluid injection device according to claim 1, wherein the piston head has a piston rod receiving chamber for receiving the piston rod therein, and wherein the internal flow channel of the piston rod, when seen in longitudinal direction (L) of said piston rod, extends beyond the location of the radial flow channel.

9. The fluid injection device according to claim 1, wherein a fluid container facing end of the flow channel has a sharp end configured for penetrating a septum of the fluid container.

10. The fluid injection device according to claim 9, wherein the flow channel is defined by a needle, the sharp end of the needle facing the fluid container.

11. The fluid injection device according to claim 1, wherein the coupler comprises snap fingers for receiving the fluid container therein.

12. The fluid injection device according to claim 1, wherein the coupler comprises a female Luer taper thread.

13. The fluid injection device according to claim 1, wherein the valve further comprises a seal ring, positioned behind the radial flow channel when seen in a longitudinal direction (L) of the piston rod, the seal ring being in contact with an inner wall of the fluid collection chamber.

14. The fluid injection device according to claim 1, wherein the valve comprises an annular rim which is in contact with an inner wall of the fluid collection chamber with at least a part of its outer circumference, the annular rim being made of said elastically deformable material and having throughflow openings, the annular rim being positioned in between the radial flow channel and the outlet nozzle in an assembled state of the fluid injection device, wherein in use a forwards movement (F) of the piston head results in a closing of the radial flow channel due to friction ($F_F$) between the annular rim and the inner wall of the fluid collection chamber, while in use a backwards movement (B) of the piston head results in an opening of the radial flow channel due to friction ($F_F$) between the annular rim and the inner wall of the fluid collection chamber.

15. A fluid injection assembly comprising a fluid injection device according to claim 1, further comprising a fluid container, the fluid container being coupled to the fluid injection device via the coupler.

16. The fluid injection assembly according to claim 15, wherein the fluid container comprises a piston head.

17. The fluid injection assembly according to claim 16, further comprising an actuator for moving the piston head of the fluid container in a direction towards the fluid injection device, said movement resulting in a flow of fluid from the fluid container towards and into the fluid collection chamber of the fluid injection device.

* * * * *